United States Patent [19]

Danielisova et al.

[11] Patent Number: 5,475,002
[45] Date of Patent: Dec. 12, 1995

[54] USE OF 1-(5-OXOHEXYL)-3-METHYL-7-N-PROPYL-XANTHINE IN VASCULAR SURGERY

[75] Inventors: Viera Danielisova, Kosice, Czechoslovakia; Ralf Kolvenbach, Düsseldorf, Germany; Hans-Peter Schubert, Apfeldorf, Germany; John Grome, Wiesbaden, Germany; Ernst J. Schneider, Bad Camberg, Germany

[73] Assignee: Hoechst Aktiengesellschaft, Frankfurt am Main, Germany

[21] Appl. No.: 155,535

[22] Filed: Nov. 22, 1993

Related U.S. Application Data

[63] Continuation of Ser. No. 886,221, May 21, 1992, abandoned.

[30] Foreign Application Priority Data

May 23, 1991 [DE] Germany ............ 41 16 799.6

[51] Int. Cl.⁶ .................................. A61K 31/52
[52] U.S. Cl. ................................................ 514/263
[58] Field of Search ................................ 514/263

[56] References Cited

U.S. PATENT DOCUMENTS 4,289,776  9/1981  Mohler et al. .................. 424/253
4,719,212  1/1988  Goto et al. ...................... 514/263

FOREIGN PATENT DOCUMENTS

2330742A1  6/1973  Germany .

OTHER PUBLICATIONS

J. DeLeo et al., Stroke, 19:1535–1539 (1988).

I. Shinoda et al., Biochemical Pharmacology, 39:1813–1816 (1990).

J. DeLeo et al., Journal of Cerebral Blood Flow and Metabolism, 7:745–751 (1987).

M. Takano et al., Cerebral Vascular Disease, vol. 5 (1985) pp. 327–341.

*Primary Examiner*—Raymond Henley, III
*Assistant Examiner*—William R. A. Jarvis
*Attorney, Agent, or Firm*—Finnegan, Henderson, Farabow, Garrett & Dunner

[57] ABSTRACT

The use of 1-(5-oxohexyl)-3-methyl-7-n-propylxanthine or of physiologically tolerated salts of this compound for the preparation of pharmaceuticals for the prophylaxis and treatment of nerve damage after interruption of the blood circulation is disclosed.

7 Claims, No Drawings

USE OF 1-(5-OXOHEXYL)-3-METHYL-7-N-PROPYL-XANTHINE IN VASCULAR SURGERY

This application is a continuation of application Ser. No. 07/886,221 filed May 21, 1992, now abandoned.

German Patent 2 330 742 discloses that 1-(5-oxohexyl)-3-methyl-7-n-propylxanthine (compound 1) is, by reason of its vasodilating action with low toxicity, suitable for the treatment of patients suffering from disturbances of arterial blood flow. Processes for preparing this compound are likewise described therein.

U.S. Pat. No. 4,719,212 describes the use of 1-(5-oxohexyl)- 3-methyl-7-n-propylxanthine for the treatment of memory disorders.

It is furthermore known that 1-(5-oxohexyl)-3-methyl-7-n-propylxanthine inhibits the uptake of adenosine in the blood vessels of the rat brain, improves the microcirculation in blood vessels and provides protection from the development of cerebral edema (Cerebral Vascular Disease 5; Ed. J. S. Meyer et al., Excerpta Medica, 1985, pages 327–341).

Vascular surgery comprises surgical treatments of vascular disorders or injuries which are carried out, in particular, in the surgical therapy of disturbances of coronary, peripheral or cerebral blood flow. The principal causes of disturbances of blood flow are functional, vasomotor vascular disorders, for example vasoconstricting disorders, for example primary and secondary vasospastic syndrome or vasodilatory disorders, for example erythromelalgia, furthermore obliterative vascular disorders in the arterial circulation, for example arteriosclerosis, diabetic angiopathy, inflammatory vascular disorders such as arteritis or endangitis, thromboses or embolisms. Arterial vascular disorders may occur in the extremities as peripheral arterial occlusive disease or in the viscera, for example as carotid occlusion, coronary heart disease, renal artery stenosis or as occlusions of larger aortic branches. In the venous circulation obliterative vascular disorders are also called deep vein thrombosis, thrombophlebitis or phlebitis. Other disturbances of blood flow are vessel-related microcirculation disorders, vascular malformations, compressions or traumatic damage to vessels.

Disadvantages of vascular surgical therapy are, related to the operation, partial or complete, short-term interruptions of the blood circulation at the site of operation, which result in more or less pronounced disturbances of function.

There has to date been no disclosure of pharmaceuticals which permit the time for symptom-free interruption of the blood circulation to be extended or which result in a significant reduction of the nerve damage caused by the interruption of the blood circulation. A prime consequence resulting from the interruption of the blood circulation is the deficient supply of oxygen, leading to metabolic disorders, in the areas affected thereby.

It has now been found that compound 1 is suitable for extending the time for a symptom-free interruption of the blood circulation, and reduces the nerve damage occurring after interruption of the blood circulation and increases the partial pressure of oxygen in the brain.

In operations in vascular surgery, such as, for example, removal of thrombi, in transplantations of kidneys or the heart or in the removal of occlusions in arteries or veins, the blood circulation must be partly or completely interrupted or greatly reduced. Depending on the duration of the operations on vessels there may then be more or less pronounced disturbances of function in the central nervous system, which may range from slight brain dysfunction to motor deficits such as, for example, paralyses. Partial or short-term interruptions of the blood circulation usually lead at the start of the interruption only to reversible damage. Tissue and nerves remain intact, with energy metabolism still maintained, a low extracellular potassium content and the possibility of complete regeneration. Surprisingly, experimental animals with short-term vascular occlusion of the abdominal aorta show after treatment with 1-(5-oxohexyl)-3-methyl-7-n-propylxanthine a rapid recovery of energy metabolism and regeneration of neuronal defects.

The invention therefore relates to the use of 1-(5-oxohexyl)- 3-methyl-7-n-propylxanthine and/or of its physiologically tolerated salts for the preparation of pharmaceuticals for the prophylaxis and treatment of nerve damage after interruption of the blood circulation.

Examples of suitable physiologically tolerated salts of 1-(5-oxohexyl)-3-methyl-7-n-propylxanthine are alkali metal, alkaline earth metal or ammonium salts, including those of physiologically tolerated organic ammonium bases.

The blood circulation can be interrupted by tourniquets or clamps in order, for example, to obtain a bloodless field for the operation, and by arterial or venous occlusion or occlusion due to embolic or thrombotic occlusions in blood vessels. Interruption of the blood circulation occurs, for example, in vascular surgical operations such as removal of thrombi, in transplantations of organs such as heart or kidney and in occlusions in arteries or veins, as occur, for example, after stroke, apoplexy or myocardial infarct. Depending on the duration of the interruption of blood circulation the nerve damage is more or less pronounced and may range from slight dysfunctions of nerves to complete nerve deficit such as, for example, paralyses. Examples of symptoms of this nerve damage which may be mentioned are: disturbances of nerve membrane potentials, mental confusion of the patients, loss of orientation, lack of responsiveness of the patient, memory disturbances, lack of concentration, motor disorders or paralyses. The blood circulation may be completely or partially interrupted and, due to this, more or less pronounced nerve damage will be observed.

The preparation of 1-(5-oxohexyl)-3-methyl-7-n-propylxanthine is carried out in a known manner (DE 23 30 742). The compound 1-(5-oxohexyl)-3-methyl-7-n-propylxanthine can be prepared, for example, by reacting an alkali metal salt of the compound of the formula I

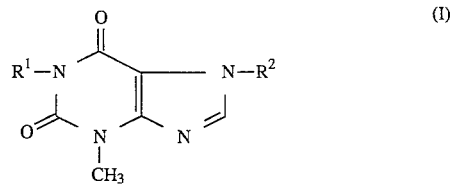

in which $R^1$ is hydrogen and $R^2$ is n-propyl group, in aqueous-organic solution with an oxoalkyl halide of the formula II

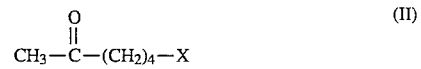

in which X is a halogen atom, such as fluorine, chlorine, bromine or iodine.

The invention also relates to pharmaceuticals which contain 1-(5-oxohexyl)-3-methyl-7-n-propylxanthine and/or at least one of its physiologically tolerated salts, in addition to pharmaceutically suitable and physiologically tolerated excipients, diluents and/or other active substances or aids.

The pharmaceuticals according to the invention can be administered orally, topically, rectally, intravenously or, where appropriate, also parenterally. Administration can take place before, after and during the interruption of the blood circulation.

Because of the pharmacological properties of the compound 1, this compound can be used in all operations in hospital or outpatient management in which the blood circulation in tissues, organs or extremities is completely or partially interrupted. This compound can furthermore be used for removal of a meniscus or diagnostic interventions when there is complete or partial interruption of the blood circulation in the affected tissue. In particular, the compound 1 is suitable for the prophylaxis and reduction of nerve damage occurring after arterial or venous occlusions of blood vessels.

The invention also relates to a process for preparing a pharmaceutical according to the invention, which comprises converting the compound 1 with a pharmaceutically suitable and physiologically tolerated vehicle and, where appropriate, other suitable active substances, additives or aids into a suitable dosage form.

Examples of suitable solid or liquid pharmaceutical forms are granules, powders, coated tablets, tablets, (micro)capsules, suppositories, syrups, solutions, suspensions, emulsions, drops or injectable solutions and products with protracted release of active substance, in whose preparation conventional auxiliaries such as excipients, disintegrants, binders, coating agents, swelling agents, glidants or lubricants, flavorings, sweeteners or solubilizers are used. Examples of frequently used aids which may be mentioned are magnesium carbonate, titanium dioxide, lactose, mannitol and other sugars, talc, lactalbumin, gelatin, starch, cellulose and its derivatives, animal and vegetable oils, polyethylene glycols and solvents such as, for example, sterile water and monohydric or polyhydric alcohols, for example glycerol.

The interruption of the blood circulation should not last much longer than 240 minutes, preferably 5 to 120 minutes, in particular 10 to 30 minutes. The time for the interruption of the blood circulation essentially depends on the partial or complete interruption and on the tissues and organs which are cut off from the blood circulation. The time limits on the interruption time can easily be established by the person skilled in the art.

The pharmaceutical products are preferably prepared and administered in dosage units, where each unit contains as active ingredient a particular dose of the compound 1 and/or at least one physiologically tolerated appropriate salt of the compound 1. In the case of solid dosage units such as tablets, capsules, coated tablets or suppositories, this dose can be up to 300 mg, but preferably about 10 to 100 mg.

The dose indicated for the treatment of a patient (70 kg) who must undergo a vascular surgical treatment is, before, during and after the operation, from 400 to 1200 mg per day and patient of the compound 1 and/or of the appropriate salts of the compound 1 in humans.

However, in some circumstances higher or lower doses may also be appropriate. The dose can be administered both by a single administration in the form of a single dosage unit or else a plurality of smaller dosage units, as well as by multiple administration of divided doses at particular intervals.

Finally, the compound 1 and/or the appropriate salts of the compound 1 can for the preparation of the abovementioned pharmaceutical forms also be formulated together with other suitable active substances, for example active substances which trap free oxygen radicals, for example 1,5-dihydro-4H-pyrazolo[3,4-d] -pyrimidin-4-one or the enzyme superoxide dismutase.

Pharmacological Tests and Results

The activity of the pharmaceuticals according to the invention was investigated on rabbits whose abdominal aorta was clamped off for a short time. This is a model for the situation equivalent to that in a vascular operation, that is to say a surgical model which, in contrast to bilateral carotid occlusion in the gerbil or 4-vessel occlusion in the rat, results in milder neuronal deficits. The effect of the pharmaceuticals according to the invention on the recovery of energy metabolism and the regeneration of neuronal deficits was observed.

EXAMPLE 1

A) Surgical Intervention 54 adult rabbits (weight 2.5–3 kg) were anesthetized by an intravenous injection of pentobarbital (5-ethyl-5-phenyl-2,4,6-trioxohexahydropyrimidine, Sigma) (30 mg/kg). Ischemia was induced by clamping off the abdominal aorta at the level of the left artery leading to the kidney for 20 or 30 minutes.

After ischemia for 20 minutes, groups of 6 experimental animals each received 1 mg/kg compound 1, 5 mg/kg compound 1, 10 mg/kg compound 1 and 20 mg/kg compound 1 by intravenous injection. After ischemia for 30 minutes, groups of 6 experimental animals each received 10 mg/kg and 20 mg/kg compound 1 by intravenous injection. Compound 1 was administered immediately after loosening the aortic clamp.

B) Arterial Blood Analysis

During the abovementioned intervention (A; 20 min. interruption of blood flow) the pH and the partial pressure of oxygen and of carbon dioxide in the left femoral artery were measured. Table 1 shows the results. In the control animals, the aorta was likewise clamped off but no pharmaceutical according to the invention was given.

TABLE 1 pH, partial pressure of oxygen ($pO_2$) and partial pressure of carbon dioxide ($pCO_2$) in the arterial blood of rabbits

| | Control animals | Compound 1 (mg/kg i.v.) | | |
|---|---|---|---|---|
| | without compound 1 | 5 | 10 | 20 |
| before interruption of blood flow | | | | |
| pH | 7.38 ± 0.03 | 7.47 ± 0.07 | 7.36 ± 0.06 | 7.41 ± 0.03 |

TABLE 1-continued pH, partial pressure of oxygen (pO$_2$) and partial pressure of carbon dioxide (pCO$_2$) in the arterial blood of rabbits

|  | Control animals | Compound 1 (mg/kg i.v.) | | |
|---|---|---|---|---|
|  | without compound 1 | 5 | 10 | 20 |
| pCO$_2$ (kPa) | 4.40 ± 0.10 | 4.94 ± 0.06 | 4.75 ± 0.12 | 5.26 ± 0.05 |
| pO$_2$ (kPa) during interruption of blood flow | 13.70 ± 0.20 | 10.17 ± 0.47 | 9.41 ± 0.15 | 10.98 ± 0.06 |
| pH | 7.44 ± 0.02 | 7.48 ± 0.02 | 7.41 ± 0.12 | 7.44 ± 0.02 |
| pCO$_2$ (kPa) | 5.10 ± 0.20 | 4.99 ± 0.16 | 4.55 ± 0.40 | 5.11 ± 0.11 |
| pO$_2$ (kPa) 5 min. recirculation | 12.80 ± 0.50 | 10.08 ± 0.06 | 9.51 ± 0.05 | 9.80 ± 0.12 |
| pH | 7.43 ± 0.01 | 7.51 ± 0.03 | 7.46 ± 0.01 | 7.43 ± 0.02 |
| pCO$_2$ (kPa) | 5.20 ± 0.20 | 4.84 ± 0.02 | 4.58 ± 0.02 | 5.23 ± 0.03 |
| pO$_2$ (kPa) 60 min. recirculation | 13.20 ± 0.40 | 10.04 ± 0.04 | 9.48 ± 0.12 | 12.25 ± 0.08 |
| pH | 7.42 ± 0.03 | 7.47 ± 0.04 | 7.50 ± 0.01 | 7.45 ± 0.01 |
| pCO$_2$ (kPa) | 5.30 ± 0.10 | 5.14 ± 0.03 | 4.80 ± 0.03 | 5.25 ± 0.05 |
| pO$_2$ (kPa) | 13.10 ± 0.40 | 10.58 ± 0.05 | 9.90 ± 0.10 | 12.38 ± 0.06 | i.v. = intravenous
Average values (n = 6) ± variation

C) Biochemical Analysis

Spinal cord was frozen with liquid nitrogen by standard methods (Anderson et al., 1980, J. Neurosurg., 52, pages 387–391). Pieces of the spinal cord (200 mg) were dissected below the 5th vertebra and only the spinal cord tissue was powdered in liquid nitrogen, and adenine nucleotides, glucose and lactate were extracted with methanol/HCl and HClO$_4$ (Folbergrova et al., 1974, Brain Res., 80, pages 265–279) and determined by fluorimetry (Lowry and Passonneau, 1972, Academic Press, New York, page 291 et seq.). The stated concentrations relate to mmol/kg wet weight of the tissue. Tables 2 and 3 summarize the results.

TABLE 2

Effects of compound 1 on the recovery of spinal cord tissue of the rabbit after 20 minutes ischemia, measured after 4 days

|  | Control animals | Compound 1 (mg/kg i.v.) | | | | |
|---|---|---|---|---|---|---|
|  | without ischemia | 0 | 1 | 5 | 10 | 20 |
| ATP | 2.334 ± 0.104 | 0.523 ± 0.038 | 1.434 ± 0.239 | 1.798 ± 0.152 | 2.344 ± 0.097 | 2.362 ± 0.106 |
| Ad | 2.635 ± 0.084 | 0.828 ± 0.031 | 1.836 ± 0.205 | 2.166 ± 0.139 | 2.729 ± 0.069 | 2.754 ± 0.112 |
| Glucose | 2.573 ± 0.155 | 0.966 ± 0.027 | 1.641 ± 0.193 | 1.640 ± 0.147 | 2.278 ± 0.085 | 2.535 ± 0.110 |
| Lactate | 1.553 ± 0.049 | 2.521 ± 0.094 | 2.740 ± 0.237 | 2.389 ± 0.328 | 1.610 ± 0.170 | 1.690 ± 0.014 |

Average values in mmol/kg wet weight (n = 6) ± variation
ATP Adenosine triphosphate
Ad Adenine nucleotides

TABLE 3

Effects of compound 1 on the recovery of spinal cord tissue of the rabbit after 30 minutes ischemia, measured after 4 days

|  | Control animals | Compound 1 (mg/kg i.v.) | | |
|---|---|---|---|---|
|  | without ischemia | 0 | 10 | 20 |
| ATP | 2.334 ± 0.104 | 0.539 ± 0.105 | 0.677 ± 0.106 | 0.993 ± 0.106 |
| Ad | 2.635 ± 0.084 | 0.990 ± .0106 | 1.134 ± 0.073 | 1.669 ± 0.120 |
| Glucose | 2.573 ± 0.155 | 0.685 ± 0.086 | 0.629 ± 0.087 | 1.240 ± 0.210 |
| Lactate | 1.553 ± 0.049 | 3.232 ± 0.155 | 2.436 ± 0.219 | 1.781 ± 0.139 |

Units of the values as in Table 2

D) Neurological Observations

The neurological functions were assessed after postoperative recovery. The assessment of the neurological deficits takes place in 3 groups:

Group 0:
No neurological deficits; the animals hop normally and recoil from visual threats.

Group 1:
The animals drag the rear legs behind them and react abnormally to visual threats; slight to severe dysfunction of intestines and bladder have been included.

Group 2:
Complete paralysis of the rear legs and no reaction to painful stimuli; severe damage to intestinal and bladder function.

The results of the neurological observations on the experimental animals with 20 min. of ischemia and 4 days of recovery are summarized in Table 4, and the results with 30 min. of ischemia and 4 days of recovery are shown in Table 5.

TABLE 4

Experimental animals with 20 minutes of ischemia and 4 days of recovery. The numbers indicate the number of animals assigned to the appropriate group

| | Group 0 | Group 1 | Group 2 |
|---|---|---|---|
| Control animals without compound 1 | — | 1 | 5 |
| 1 mg/kg compound 1 | 1 | 3 | 2 |
| 5 mg/kg compound 1 | 1 | 4 | 1 |
| 10 mg/kg compound 1 | 5 | 1 | — |
| 20 mg/kg compound 1 | 5 | 1 | — |

TABLE 5

Experimental animals with 30 minutes of ischemia and 4 days of recovery

| | Group 0 | Group 1 | Group 2 |
|---|---|---|---|
| Control animals without compound 1 | — | — | 6 |
| 10 mg/kg compound 1 | — | 1 | 5 |
| 20 mg/kg compound 1 | — | 5 | 1 |

EXAMPLE 2

Preparation of 1-(5-oxohexyl)-3-methyl-7-n-propylxanthine (compound 1)

437.2 g of 3-methyl-7-propylxanthine are suspended in a mixture of 240 g of methanol and 321 g of water and induced to dissolve at elevated temperature with 160 g of 50% strength sodium hydroxide solution, and subsequently at the boiling point 358 g of 1-bromo-5-hexanone are added and the mixture is heated to reflux for 4½ hours. After cooling, unreacted 3-methyl-7-propylxanthine is separated off and the alcohol is removed by distillation. The aqueous solution is adjusted to pH 11 with sodium hydroxide solution and extracted with methylene chloride. 1-(5-Oxohexyl)-3-methyl-7-propylxanthine is obtained with melting point 69°–70° C. in approximately 90% yield (based on reacted 3-methyl-7-propylxanthine) from the residue of the methylene chloride solution after recrystallization from 5.2 of diisopropyl ether.

We claim:

1. A method for the treatment or prophylaxis of reversible nerve damage caused by an interruption of blood circulation in a mammal and for the recovery of energy metabolism comprising administering to a mammal in need thereof an effective amount of a pharmaceutical composition comprising 1-(5-oxohexyl)-3-methyl-7-n-propylxanthine, or at least one of its physiologically tolerated salts together with a pharmaceutically suitable and physiologically tolerated vehicle.

2. The method of claim 1, wherein said interruption of blood circulation is due to surgery, and the length of said surgery is able to be extended for 5 to 240 minutes by said method.

3. The method of claim 2, wherein the length of said surgery is able to be extended for 10 to 30 minutes by said method.

4. The method of claim 1, wherein said interruption of blood circulation is due to arterial or venous occlusion of blood vessels.

5. The method of claim 1, wherein said interruption of blood circulation occurs after vascular surgery.

6. The method of claim 1, wherein the partial pressure of oxygen in the brain is increased thereby.

7. The method of claim 1, wherein said pharmaceutical composition is administered before, after or during a surgical operation in which there is an interruption of blood circulation.

* * * * *